United States Patent [19]
Thomson

[11] 4,426,446
[45] Jan. 17, 1984

[54] LEUCOCYTE ADHERENCE INHIBITION ASSAY FOR DETECTION OF CANCER

[75] Inventor: David M. P. Thomson, Monte Royal, Canada

[73] Assignee: Hoffmann-La Roche Inc., Nutley, N.J.

[21] Appl. No.: 231,063

[22] Filed: Feb. 3, 1981

[51] Int. Cl.[3] .................... G01N 33/52; G01N 33/54; G01N 33/88

[52] U.S. Cl. .......................................... 435/7; 435/4; 436/63; 436/64; 436/519; 436/800; 436/813

[58] Field of Search .................... 435/4, 6, 7, 29, 240, 435/810, 296; 424/7, 8, 12; 23/230 B; 436/63, 64, 800, 808, 810, 813, 519, 501, 506

[56] References Cited

U.S. PATENT DOCUMENTS

| | | | |
|---|---|---|---|
| 3,999,944 | 12/1976 | Grosser et al. | 436/519 |
| 4,060,457 | 11/1977 | Iizuka et al. | 435/296 |
| 4,094,745 | 6/1978 | Scholefield et al. | 435/7 |
| 4,254,219 | 3/1981 | Fullerton | 435/7 |

OTHER PUBLICATIONS

Rose et al., *Methods in Immunodiagnosis,* 2nd ed., John Wiley & Sons, N.Y. (1980), pp. 39–43.

Kalafut et al., "Application of the Indirect Tube LAI Assay in the Study of Cell–Medicated Immunity in Rats Immunized with B77 Tumor Cells", *Chem. Absts.,* vol. 94, No. 19, (1981), p. 469, Absts. #154656w.

Howell, et al., "Characterization of Murine Tumor–Associated Antigens by the Microleukocyte Adherence Inhibition Assay", *Chem. Absts.,* vol. 90, No. 13 (1979), p. 418 Absts. #101755p.

Thomson, et al., "Evidence for the Expression of Human Tumor Specific Antigens Associated with $B_2$–Microglobulin in Human Cancer and in some Colon Indenomes and Benign Breast Lesions", *Chem. Absts.,* vol. 90, No. 15, (1979), pp. 482, 483 Absts. #119610x.

Powell et al., "Antigenic Specificity and Cellular Mechanisms in Leukocyte Adherence Inhibition Analysis of Immunity to Simple Proteins and Hapten–Protein Conjugates", *Chem. Absts.,* vol. 90, No. 15, (1979), p. 467 Absts. #119477.

Bryant et al., "The Effect of 3′,5′–Adenosine Monophosphate Granulocyte Adhesion", *J. Chem. Invest.,* vol. 54 (1974), pp. 1241–1244.

Powell et al., "Leukocyte–Adherence Inhibition: A Specific Assay of Cell Medicated Immunity Dependent on Lymphokine Medicated Collaboration between T Lymphocytes", *J. Immunology,* vol. 120, No. 6, (1978), pp. 1957–1966.

*Primary Examiner*—Sidney Marantz
*Attorney, Agent, or Firm*—Jon S. Saxe; George M. Gould; John J. Maitner

[57] ABSTRACT

Methods for carrying the leucocyte adherence inhibition (LAI) assay for detecting the presence of cancer in responsive patients. One aspect of the invention utilizes incubation with agents which maximize the intracellular cycle 3′,5′-adenosine monophosphate (cAMP) levels in the leucocytes as a means to expand the percentage of responding subjects in different cancers. A second aspect utilizes measurement of extracted, vital cell dye to avoid the need of counting the adhering or non-adhering leucocytes.

12 Claims, No Drawings

LEUCOCYTE ADHERENCE INHIBITION ASSAY FOR DETECTION OF CANCER

BACKGROUND OF THE INVENTION

The existence of tumor neoantigens in experimental animal tumors has been known for many years. There has been increasing evidence that human cancers, too, express tumor neoantigens that are recognized by humoral and cellular reactions of the host to the cancer cell or its products, in in vitro assays. See generally Shuster et al., Prog. Exp. Tumor Res., 25 89 (1980). This organ-specific neoantigen is shared by all cancers arising from the organ, so that patients with similar cancers will respond to each others cancer neoantigen.

It seems that human cancers may stimulate the hosts' immunologic response. Some prostatic carcinoma patients, for example, respond with a delayed cutaneous hypersensitivity reaction to injected tumor extract of the same histogenesis. Cell mediated cytotoxicity to the cancer was shown to exist in patients with prostatic carcinoma, especially those with stage B lesions.

With the discovery of the phenomenon of leucocyte adherence inhibition (LAI) a comparatively simple in vitro technique for measuring the hosts' antitumor immune response became available. See for example U.S. Pat. No. 3,999,944, issued Dec. 28, 1976 which describes the tube LAI assay for detection of the presence or absence of breast cancer in subjects. The extensions of the tube LAI to other tumor disease states is described in U.S. patent Ser. No. 68,378, filed Aug. 21, 1979, inventors Marti et al. Specific tumors disclosed include malignant melanoma, bladder carcinoma, ovarian cancer and cervical cancer.

The LAI assay is based on the observation that leucocytes from patients with cancer after being incubated in vitro with extracts of cancer tissue of the same organ and histogenesis, lose their former ability to adhere to glass, by binding to the tumor antigen.

One of the limitations of the LAI assay was the fact that substantial percentages of advanced cancer patients with various types of cancers do not have a measurable antitumor response and thus produce a false negative in the test. This fact limits the practical utility of the LAI in providing a broad scale clinical assay for cancer.

Failure of substantial numbers of cancer patients to express an antitumor immune response is particularly exemplified by the situation with prostatic carcinoma althought it can also be documented with breast, lung, stomach, pancreas, colon, bladder and melanoma cancers.

It has been found, for example, that relatively few patients (14%) with prostatic carcinoma had a measurable antitumor response. However, their tube LAI-positive responses were stastically greater than control subjects (1.5%) with or without benign prostatic hyperplasia (BPH).

The tube LAI procedure has also been previously described in detail by Grosser and Thomson, Cancer Res., 35 2571 (1975). In brief outline the procedure utilizes samples each containing B 0.1 ml of a peripheral blood leucocyte suspension ($1\times10^7$ cells/ml) which are incubated with either specific or nonspecific tumor antigen extracts ($\sim100$ $\mu$g in 0.1 ml). The tubes are incubated horizontally for 2 hours at 37° C. in a 5% $CO_2$ humidified atmosphere. After 2 hours, the tubes are carefully placed vertically, and a sample of the nonadherent cells are counted by image analysis driven by computerized-linked instruments. The difference in non-adherent cells in the presence of cancer and a control tumor extract is expressed as a nonadherence index (NAI):

$$NAI = \frac{\text{Number of Nonadherent cells in presence of specific antigen} - \text{Number of Nonadherent cells in presence of nonspecific antigen}}{\text{Number of Nonadherent cells in the presence of nonspecific antigen}} \times 100$$

Based on clinical experience with the assay it was determined that NAI's of 30 or greater are considered positive since greater than 95% of the patients without the specific cancer had NAI's of 30 or less.

The necessity in the above methodology that the nonadherent cells be counted by an automated computer linked counter is a further obstacle to the methodology becoming a widely accepted procedure since the cost of such instrumentation is prohibitive for most laboratories and requires the services of a highly trained technician; another expensive, acceptance limiting burden on the methodology.

DESCRIPTION OF THE INVENTION

The present invention relates to improvements in carrying out the LAI assay which result in a simpler, more efficient procedure which does not require sophisticated instrumentation or the services of highly trained technicians to carry out. In addition, the improved LAI of the present invention provides and can be used to estimate the tumor burden.

In one aspect of the present invention, greatly enhanced responsiveness of peripheral blood leucocytes (PBL) samples can be achieved by incubating such samples with an agent which maximizes the intracellular cAMP levels in such leucocytes. Suitable agents for this purpose include compounds which are known to elevate cAMP levels in leucocytes either by stimulating its synthesis or preventing its destruction or combinations thereof.

Compounds which are useful to stimulate synthesis of cAMP in cells include the prostaglandins, either natural or synthetic analogs and prostacyclins. Preferred cAMP synthesis stimulating compounds include prostaglandin $E_2(PGE_2)$ and synthetic analogs such as the compounds of the formula

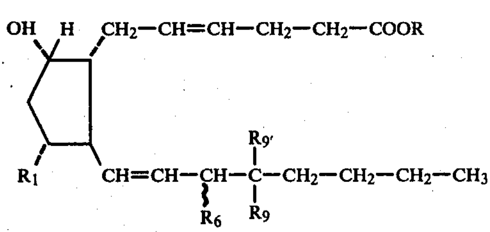

wherein R is hydrogen or lower alkyl; $R_1$ is hydrogen, lower alkyl, lower alkoxycarbonyl, $—CH_2OR_8$, carboxy or

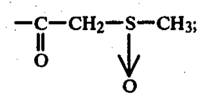

$R_6$ is hydroxy or hydroxy protected with a hydrolyzable ether or ester group; $R_8$ is hydrogen or lower alkyl, $R_9$ is hydrogen, lower alkyl or fluoro; $R_9'$ is hydrogen or lower alkyl; and the dotted bond can be optimally hydrogenated and enantiomers or racemates thereof as disclosed in U.S. patent application Ser. No. 25,972 filed Apr. 2, 1979, entitled "11-Substituted Prostaglandins", inventors George William Holland et al.

Preferred compounds are obtained when R is hydrogen, $R_1$ is lower alkyl and $R_6$ is hydroxy.

A particularly preferred compound from this group for use in the practice of the present invention is nat. 11 R-methyl-16 R-fluoro-15.R-hydroxy-9S-hydroxyprosta-cis-6-trans-13-dienoic acid which, in alternative nomenclature, employed in the aforesaid application is referred to as 7 [3 alpha-methyl-5 alpha-hydroxy-2 beta (3 alpha-hydroxy-4 fluoro-1-trans-octenyl)-1-alpha-cyclopentyl]-cis-5-heptenoic acid.

The terms "lower alkyl" "lower alkoxycarbonyl" and "hydrolyzable ether or ester group" are intended to have the meaning and scope provided to such terms in the aforesaid U.S. patent application Ser. No. 25,972. Other cAMP synthesis stimulators such as aminophylline may be used in conjunction with the aforesaid prostaglandins, preferably in about equimolar concentration.

Additional prostaglandin compounds useful to stimulate synthesis of cAMP in cells include compounds of the formula

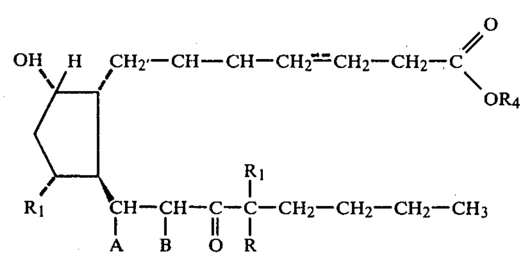

wherein A and B are individually hydrogen or form a carbon to carbon bond, $R_4$ is hydrogen or lower alkyl; $R_1$ is hydrogen or lower alkyl; R' is fluoro, lower alkyl or trifluoromethyl; R is hydrogen, fluoro or lower alkyl; and the dotted bond can be optionally hydrogenated which are disclosed in U.S. Pat. No. 4,212,993, issued July 15, 1980.

Preferred compounds are obtained when A and B form a double bond, $R_4$ is hydrogen, $R_1$ is lower alkyl, R' is fluoro and R is hydrogen and the dotted line is a double bond.

A particularly preferred compound from this group for use in the practice of the present invention is nat. 11R-methyl-16R-fluoro-9,15-dioxoprosta-cis-5-trans-13-dienoic acid.

Compounds which are useful in the prevention of cAMP destruction in lymphocytes include the phosphodiesterase inhibitors. Preferred phosphodiesterase inhibitors include a class of substituted benzylimidazolidenones which are disclosed in U.S. Pat. No. 3,636,039, issued Jan. 18, 1972. A particularly preferred compound of this group is d,l-4-(3-isopropoxy-4-methoxy-benzyl)-2-imidazolidinone.

The incubation is conveniently carried out for a short period such as from 2 to 5 minutes at room temperature.

It has further been found that the concentration of the agent which is used in the preincubation to maximize cAMP levels in the lymphocyte samples is critical. Thus, for example, when prostaglandin $E_2$ is utilized in the preincubation with lymphocytes from prostatic cancer patients it was found that molar concentrations of $10^{-4}$ and more, or $10^{-7}$ and less, did not stimulate a positive response while a positive reponse was achieved by preincubation with molar concentrations of $10^{-5}$ and $10^{-6}$ ($10^{-5}$ providing the maximum response). The critical molar concentration for any agent utilized in the practice of the present invention with any lymphocyte sample from different types of cancer can be ascertained by simple titration experiments using varying molar concentrations of the agent with samples from a single lymphocyte source and determining the non-adherence index. Suitable sources of lymphocytes from other cancers include breast, lung, stomach, pancreas, colon, bladder and melanoma cancers.

In a further aspect of the present invention the determination of the non-adherence index is simplified by utilizing a vital cell dye which selectively binds to living leucocytes to stain either the adhering or non-adhering cells. Instead of counting the individual adhering or non-adhering cells by image analysis driven by computerized-linked instruments as previously utilized, it is possible, by extracting the dye from the separated adhering or non-adhering cells and measuring the optical absorption of the extracted solution, in a spectrophotomer to correlate the resulting reading with values obtained from known quantities of cells to thereby determine the number of non-adhering cells which number is used in the computation of the NAI as described above. Such procedure simplifies the equipment needed for carrying out the LAI and allows one to employ a laboratory technician for this task rather than a trained specialist.

Suitable dyes for use in this aspect of the present invention include those that will stain viable leucocytes and which are extractable in either acid or base without affecting the dye color. Examples of useful dyes in the practice of the present invention include methylene blue, nonspecific esterase and neutral red. A preferred vital cell dye is methylene blue which can be extracted from the test cells by using a dilute aqueous mineral acid such as dilute hydrochloric acid.

While it is desirable to utilize both aspects of the present invention in combination to achieve the maximum benefits to be derived from these improvements in methodology, it is also possible to employ either of these aspects independently of each other.

The improved LAI of the present invention can be conveniently carried out utilizing reagents contained in kit form. Such a kit comprises the following:

- a vial containing a cancer antigen to be assayed sufficient for a multiplicity of tests;
- a vial containing an unrelated cancer antigen sufficient for a multiplicity of tests;
- a vial containing a sufficient amount of an agent which maximizes the cAMP levels in test leucocytes for a multiplicity of tests; and/or
- a vial containing a sufficient amount of a vital cell dye.

The present invention is further illustrated by the following Examples.

EXAMPLE 1

Materials and Methods

Patients and controls:

In a clinical study 37 patients with prostatic carcinoma, ranging in age from 65 to 72 years, were tested: 3 with Stage A, 6 with Stage B, 5 with Stage C, and 23 with Stage D. The staging was in accordance with Whitmore's classification, Cancer 32, 1104 (1973). Fifty-seven patients with histologically diagnosed BPH were studied and included among the control group; they were tested before surgery to correlate the LAI results with latent carcinoma (Stage A) found from transurethral resection and retropubic prostatectomy specimens. Other control subjects included the following: 22 patients with benign genitourinary (GU) disease other than BPH, 8 patients with genitourinary malignancy other than prostatic carcinoma, 29 patients with benign diseases other than the genitourinary system, and 12 patients with malignant diseases other than the genitourinary system. None of the patients had received chemotherapy or radiation therapy at the time of the study.

Tissue extracts:

Prostatic carcinoma extract was prepared from malignant prostate tissue that was removed from metastatic lesions of the liver and retroperitoneal lymph nodes of fresh autopsy material. Similarly, the nonspecific cancer extracts were lung carcinoma and malignant melanoma, metastatic to the liver. The tumor extracts were prepared, titrated, and diluted optimumly for the LAI assay as described previously by Grosser and Thomson, Cancer Res., 35, 2571 (1975).

Tube LAI assay:

The test was performed as previously described in detail, by Grosser and Thomson, supra. Briefly, 0.1 ml of a peripheral blood leucocyte suspension ($1\times10^7$/ml) was incubated with both specific (prostatic carcinoma) and nonspecific (lung carcinoma or malignant melanoma) tumor antigen extracts ($\simeq$100 $\mu$g in 0.1 ml). The tubes were incubated horizontally for 2 hours at 37° C. in a 5% $CO_2$ humidified atmosphere. After 2 hours, the tubes were carefully placed vertically, and a sample of the non-adherent cells were counted by image analysis driven by computerized-linked instruments. The difference in non-adherent cells in the presence of prostatic carcinoma and a control tumor extract was expressed as a non-adherence index:

$$NAI = \frac{\text{Non-adherent cells in presence of specific antigen} - \text{Nonadherent cells in presence of nonspecific antigen}}{\text{Non-adherent cells in the presence of nonspecific antigen}} \times 100$$

NAIs of $\geqq$30 were considered as positive because previous results showed that >95% of patients without the specific cancer had NAIs >30.

Tube LAI assay with Prostaglandin $E_2$($PGE_2$):

The laucocytes were tested in the tube LAI assay with and without preincubating the cells with $PGE_2$. One portion of the cell suspension was plated in LAI assay as described by Grosser and Thomson. The other portion of the cell suspension was incubated in 0.5 ml of Medium 199 containing $PGE_2$($10^{-6}$ M) for 5 minutes. The concentration of $PGE_2$ used was critical, for $10^{-4}$ and more, or $10^{-7}$ and less, did not stimulate a positive response. Then the cells were diluted with Medium 199 to reach the appropriate cell concentration of $1\times10^7$/ml. The cells were plated in the tubes, and the assay was conducted as previously described by Grosser and Thomson.

Results

Tube LAI assay in prostatic carcinoma and control patients:

The NAIs of each patient tested were determined. Leucocytes from 2 out of 23 (8%) patients with Stage D and 1 out of 5 (20%) patients with Stage C were reactive. Of Stage B patients only 1 of 6 (16%) reacted. All 3 patients with Stage A had their cancer found incidentally in surgical specimens for BPH (5%, 3/60); one of the 3 was LAI positive. There were 9 patients with localized disease (Stage A and B) of whom only 2 (22%) reacted compared to 28 patients with advanced stage of disease (Stage C and D) of whom 3 (11%) reacted.

Although the number of LAI-positive patients with prostatic carcinoma was small (14%, 5/37), the difference from the control group was statistically significant (Chi square, P<0.05). Table 1 shows that the mean NAI of prostatic carcinoma patients was 11 and differed from the mean NAI of 2 for the control subjects. (Student's independent t test, P<0.02). Naught of the 57 patients with BPH were reactive to the malignant prostate extract. Of the 71 other controls tested, 2 were positive (2.6%); one was a woman and the other was not retested. Because of the small number of patients tested in each stage of the disease, no statistical significant difference was observed between the different stages of prostatic cancer.

TABLE 1

Summary of patients tested by tube LAI for reactivity to Prostatic Carcinoma extract.

| Patients studied | No. | +NAI's No. (%) | Mean NAI+ |
|---|---|---|---|
| Prostatic carcinoma: | 37** | 5(14)** | 11 |
| Stage A | 3 | 1(33) | 12 |
| Stage B | 6 | 1(16) | 16 |
| Stage C | 5 | 1(20) | 11 |
| Stage D | 23 | 2(8) | 4 |
| Other GU. disease*: | 87** | 0(0)** | 1 |
| BPH | 57 | 0(0) | −0.5 |
| Other benign GU. disease | 22 | 0(0) | −1 |
| Other malignant GU. disease | 8 | 0(0) | 3.5 |
| Non-GU. disease: | 41** | 2(4)** | 3 |
| Benign | 29 | 2(7) | 9 |
| Malignant | 12 | 0(0) | −3 |

*Overall mean NAI in control patients was 2.

**A comparison of the LAI positive and negative patients in prostatic carcinoma and controls by Chi square, $\chi^2 = 4.39$, thus $P < 0.05$.

+The mean NAIs of prostatic carcinoma patients and control subjects were compared by Student's independent t test and is significant $P < 0.02$ Tube LAI assay and $PGE_2$ stimulation:

The NAI results using leucocytes with and without $PGE_2$ stimulation were compared. Of the 18 patients with prostatic carcinoma, 3 were positive without $PGE_2$, and these patients remained LAI positive after $PGE_2$ stimulation. The other 14 prostatic carcinoma patients were LAI negative, but converted to positive with $PGE_2$ stimulation. Overall, that means 61% (11/18) of patients with prostatic carcinoma were LAI-positive. Another 35 control patients, 18 of whom had BPH, had their leucocytes stimulated with $PGE_2$. Only one (3%) patient had a positive response with $PGE_2$ stimulation; when retested a week later, this patient with BPH was LAI-negative. In the control group, the mean NAI of 1.2±1.5 without $PGE_2$ stimulation was not statistically significantly different (Student's dependent t test) from the mean NAI of 1.8±1.7 after $PGE_2$ stimulation. By contrast, the mean NAI of 28±0.4 for prostatic carcinoma patients with $PGE_2$ stimulation was significantly different from the mean NAI of 9.5±0.5 without $PGE_2$ stimulation. (Student's dependent t test, P 0.005).

Table 2 shows that 61% of patients with prostatic carcinoma were LAI-positive with $PGE_2$ stimulation, and this was significantly different ($P<0.005$) from the control subjects with 3% LAI-positive.

TABLE 2

LAI results with $PGE_2$ stimulation in Prostatic Carcinoma patients and control patients.

| | No. | (+) NAI's No. (%) |
|---|---|---|
| Prostatic carcinoma: | 18* | 11(61)* |
| Stage A | 1 | 9(0) |
| Stage B | 3 | 3(100) |
| Stage C | 2 | 2(100) |
| Stage D | 12 | 6(50) |
| Controls: | 35* | 1(3)* |
| BPH | 18 | 1(5) |
| Other Disease | 17 | 0(0) |

*A comparison of LAI positive and negative in prostatic carcinoma and controls by Chi square, $\chi^2 = 19.8$, thus $P < 0.005$ Organ-specific neoantigen:

Twenty patients with cancers other than prostate were tested for reactivity to the prostatic carcinoma extract, and none reacted. These patients had cancer of the kidney, bladder, testis, colon, breast and pancreas. Conversely, leucocytes from prostatic carcinoma patients were tested against extracts of bladder, colon, and pancrease carcinoma, and none reacted to these cancer extracts. No patients with BPH reacted to the prostatic carcinoma extract, and when the tissue from BPH was used as an extract, none of the LAI-positive prostatic carcinoma patients reacted to the BPH extract.

LAI and serum prostatic acid phosphatase (PAP) by radioimmunoassay:

In 13 prostatic carcinoma patients with various stages of the disease both PAP and LAI were performed in samples drawn the same day. The patients were divided into those with PAP within normal or above normal limits. In a group of 8 patients the mean PAP level of 2.7 ng/ml was within normal limits (N=1.2-5.7 ng/ml), and in this group the mean NAI was 19. By contrast, in the other group of 5 patients the mean PAP level was elevated to 13.4 ng/ml, and they had a mean NAI of 0.2.

When the patients age and their LAI response was compared, there was no difference in the LAI response of young or old patients.

Discussion

It has now been found that prostatic carcinoma patients express an antitumor immune response. Although few patients (14%) with prostatic carcinoma had a measureable antitumor response, their LAI-positive responses were statistically greater than the control subjects (1.5%) with or without BPH.

Because most patients with prostatic carcinoma seldom reacted in the tube LAI assay, the possible role of the patients, age and the tumor burden on the LAI response was examined. There was no difference in the LAI response of patients either young or old; thus, the patient's age did not explain the impaired antitumor response. When the bulk of tumor was estimated by measuring serum PAP by radioimmunoassay, patients with elevated values were observed to have low NAIs, demonstrating a lack of an antitumor immune response. On the other hand, patients with similar clinical stages of prostatic carcinoma, but low serum PAP levels, had high NAIs; hence, they expressed an antitumor immune response The low incidence of antitumor immune responses detected in patients with prostatic carcinoma may reflect the affect of the tumor burden which, in most patients, is large enough to suppress the response by shedding tumor antigen, systemically.

There may be other reasons, of course, why patients with prostatic carcinoma seldom react in the tube LAI assay. It could be that the tumor extracts may not possess good antigenic activity. This possibility can not be entirely excluded, but tumor from two different sources gave similar results. Moreover, if the antigenic activity of the extracts was poor, it seems unlikely that $PGE_2$ stimulation of the leucocytes would have intensified the LAI response.

It seems, therefore, that the impaired LAI response of prostatic carcinoma patients reflects a functional defect in the responding leucocytes. This is supported by the fact that 61% of patients in the above study with prostatic carcinoma showed a positive LAI response after $PGE_2$ leucocyte stimulation. The $PGE_2$ stimulation was specific, for only 3% of controls were LAI positive. Also the mean NAI of control subjects did not change after $PGE_2$ stimulation, but the mean NAI of prostatic carcinoma patients rose dramatically.

$PGE_2$, an extracellular mediator, binds to cell-surface receptors that engages and activates the adenylate-cyclase enzyme to enhance intracellular levels of cyclic 3',5'-adenosine monophosphate (cAMP). How the raised intracellular levels of cAMP restore leucocyte antitumor reactivity is not known, at this moment.

Analogous to other systems, in particular the mast cell, it seems probable that the cytophilic antitumor antibody on the membrane of leucocytes of prostatic carcinoma patients is cross-linked by antigen which is transduced into information useful to the cell. The transduction appears to involve the opening of calcium channels in the cell membrane, allowing calcium to enter the cell; this affects the polarization of the cell and may be responsible, in part, for the phenomenon of LAI. Increased intracellular levels of cAMP inhibit calcium gate formation, allowing the cell membrane to return to its normal polarized state. It seems possible that leucocytes from prostatic carcinoma patients, having encountered repeatedly tumor antigen in vivo, already have altered membrane potential, and the $PGE_2$ stimulation, by raising intracellular cAMP, inhibits calcium entry and helps the cell membrane to rapidly return to its normal polarized state. So when the leucocytes bind again tumor antigen in vitro, the transduction will open calcium channels, and the rise in free calcium in the cell will act, once more, to stimulate programmed cellular events; these events, including the changing membrane potential of the cells, mediate the phenomenon of LAI.

Bhatti et al., J. Retic. Soc. 25, 389 (1979); Eur. J. Cancer 15, 133 (1979) and Evans et al., Proc. R. Soc. Med. 70, 417 (1977) have reported that PBL of 77% and 89% of prostate carcinoma patients reacted prostatic carcinoma extracts in the tube LAI assay. The reason why our results are different is not clear. But Bhatti et al. seem to have calculated the results of individual patients on the basis of incubating cells with one antigen rather than comparing leucocyte non-adherence of each patient to the specific and nonspecific antigens. It is believed to be essential, however, to compare the *differ-*

*ence* in leucocyte non-adherence to the specific and nonspecific tumor extracts because leucocytes from advanced cancer patients, having already encountered tumor antigen in vitro, show enhanced non-adherence to glass with specific but also to nonspecific antigens.

The cancer antigen expressed by the prostate carcinoma is an organ-specific neoantigen, for patients with carcinoma other than prostate did not react to the prostatic carcinoma, nor did prostatic carcinoma patients react to extracts of other carcinomas. The antigen does not seem to be a normal tissue antigen, but is a neoantigen; for prostatic carcinoma patients did not react to an extract of benign prostatic hyperplasia, and patients with BPH showed no reactivity to prostatic carcinoma extracts. This differs from the findings of Avid et al., Urology 5, 122 (1975).

In the present study, more patients with early carcinoma showed a positive LAI response than did patients with late carcinoma, but the difference was not statistically significant due to the small number of patients responding in both groups.

In summary, prostatic carcinoma patients seldom react in the tube LAI assay. These patients may have a sufficient bulk of carcinoma, whether clinically detectable or not, to release systemically an excess or tumor antigen. This impairs the detection of the host's antitumor response in vitro because the leucocytes have already bound tumor antigen in vivo. Because $PGE_2$ has the ability to reverse the functional defect of the leucocytes produced by the circulating tumor antigen, it now makes it possible to detect an antitumor immune response in a greater number of patients with prostatic carcinoma.

It is understood that the discussion concerning the scientific theories upon which this aspect of the present invention is believed to be based is for purposes of illustration and exemplification only and should not be considered limiting in any way.

EXAMPLE 2

The LAI procedure of Example 1 was repeated with samples from prostatic carcinoma patients using a preincubation with a solution comprising $10^{-5.5}$ M $PGE_2$ and $10^{-5}$ M aminophyllin provided mean NAI values above 60.

EXAMPLE 3

The LAI procedure of Example 1 was repeated with samples from prostatic carcinoma patients using a preincubation with a solution comprising $10^{-5}$ M d,l-4-(3-isopropoxy-4-methoxybenzyl)-2-imidazolidinone provided mean NAI values above 65.

EXAMPLE 4

The LAI procedure of Example 1 was repeated with samples from prostatic carcinoma patients using a preincubation with a solution comprising $10^{-6}$ M nat. 11R-methyl-16R-fluoro-15R-hydroxy-9S-hydroxyprosta-cis-6-trans-13-dienoic acid provided mean NAI values above 65. However, similar tests run with nat. 11R methyl-16R-fluoro-15R-hydroxy 9-oxoprosta-cis-6-trans-13-dienoic acid at concentrations of $10^{-6}$ M, $10^{-7}$ M, $10^{-8}$ M, $10^{-9}$ M and $10^{-10}$ M yielded mean NAI values below 30 in all cases thus indicating that the latter compound was inactive.

EXAMPLE 5

The LAI procedure of Example 1 was repeated with samples from prostatic carcinoma patients using a preincubation with a solution comprising $10^{-7}$ M nat. 11R-methyl-16-R-fluoro-9,15-dioxoprosta-cis-5-trans-13-dienoic acid provided mean NAI values above 55. Use of $10^{-6}$ M in parallel runs provided mean NAI values below 30.

I claim:

1. In a tube leucocyte adherence inhibition assay for the detection of cancer in a subject wherein samples of a known amount of peripheral blood leucocyte are incubated horizontally with either specific or nonspecific tumor antigen extracts in test tubes, the test tubes are carefully placed vertically and the non-adherent cells are counted for each sample and the non-adherent index determined, the improvement which comprises:
   (a) preincubating said peripheral blood leucocytes with an effective concentration of an agent which maximizes cAMP levels in leucocytes to thereby heighten the LAI response of such leucocytes; and
   (b) treating said adherent or non-adherent cells with a vital cell dye selected from the group consisting of methylene blue, nonspecific esterase and neutral red, separating said adherent or non-adherent cells, extracting said dye, determining the optical adsorption of said extracted solution which is directly proportional to the number of cells present thus providing the number of adhering or non-adhering cells without the necessity of optically counting such cell directly wherein said agent which maximizes cAMP levels in the leucocytes is a prostaglandin compound which stimulates leucocyte cAMP or a phosphodiesterase inhibitor which prevents cAMP destruction.

2. In a tube leucocyte adherence inhibition assay for the detection of cancer in a subject wherein samples of a known amount of peripheral blood leucocytes are incubated horizontally with either specific or nonspecific tumor antigen extracts in test tubes, the tubes are carefully placed vertically and the non-adherent cells are counted for each sample and the non-adherent index determined, the improvement which comprises preincubating said peripheral blood leucocytes with an effective concentration of an agent which maximizes cAMP levels in leucocytes to thereby heighten the LAI response of such leucocytes wherein said agent which maximizes cAMP levels in the leucocytes is a prostaglandin compound which stimulates leucocyte cAMP or a phosphodiesterase inhibitor which prevents cAMP destruction.

3. In a tube leucocyte adherence inhibition assay for the detection of cancer in a subject wherein samples of a known amount of peripheral blood leucocytes are incubated horizontally with either specific or nonspecific tumor antigen extracts in test tubes, the tubes are carefully placed vertically and the non-adherent cells are counted for each sample and the non-adherent index determined, the improvement which comprises treating said adherent or non-adherent cells with a vital cell dye selected from the group consisting of methylene blue, nonspecific esterase and neutral red, separating said adherent or non-adherent cells, extracting said dye, determining the optical absorption of said extracted solution which is directly proportional to the number of cells present thereby providing the number of adhering or non-adhering cells without the necessity of optically counting such cells directly.

4. The leucocyte adherence inhibition assay of claims 1, 2 or 3 wherein the specific antigen is derived from a member selected from the group consisting of a breast, lung, stomach, pancreas, colon, prostate, bladder and melanoma cancer.

5. The leucocyte adherence inhibition assay of claim 1 or 2 wherein said prostaglandin is prostaglandin $E_2$ present in the preincubation medium in a molar concentration of between about $10^{-5}$ to $10^{-6}$.

6. The leucocytes adherence inhibition assay of claim 5 wherein said prostaglandin is prostaglandin $E_2$ present in combination with aminophyllin both at a molar concentration of about $10^{-5}$.

7. The leucocyte adherence inhibition assay of claim 1 or 2 wherein said prostaglandin is nat. 11R-methyl-16R-fluoro-15R-hydroxy-9S-hydroxyprosta-cis-6-trans-13-dienoic acid.

8. The leucocyte adherence inhibition assay of claim 1 or 2 wherein said agent is a substituted benzylimidazolidione phosphodiesterase inhibitor.

9. The leucocyte adherence inhibition assay of claim 8 wherein said agent is d,l-4-(3-isopropoxy-4-methoxybenzyl)-2-imidazolidinone.

10. The leucocyte adherence inhibition assay of claims 1 or 3 wherein said vital cell dye is methylene blue.

11. The leucocyte adherence inhibition assay of claim 10 wherein said vital cell dye is extracted with dilute hydrochloric acid.

12. The leukocyte adherence inhibition assay of claim 1 or 2 wherein said prostaglandin is nat. 11R-methyl-16R fluoro-9,15-dioxoprosta-cis-5-trans-13-dienoic acid.

* * * * *